United States Patent [19]
Goeddel et al.

[11] Patent Number: 5,563,039
[45] Date of Patent: Oct. 8, 1996

[54] TNF RECEPTOR-ASSOCIATED INTRACELLULAR SIGNALING PROTEINS AND METHODS OF USE

[75] Inventors: David V. Goeddel; Hailing Hsu, both of South San Francisco, Calif.

[73] Assignee: Tularik, Inc., So. San Francisco, Calif.

[21] Appl. No.: 414,625

[22] Filed: Mar. 31, 1995

[51] Int. Cl.$^6$ .......... C07K 14/46; C12N 15/12; G01N 33/566

[52] U.S. Cl. .......... 435/7.1; 435/6; 435/69.1; 435/252.3; 435/320.1; 436/501; 530/350; 530/300

[58] Field of Search .......... 435/6, 7.1, 69.1, 435/252.3, 320.1; 436/501; 530/350, 300; 536/23.5

[56] References Cited

PUBLICATIONS

Van Arsdale and Ware (1994) J. Immunology 153:3043–3050.
Rothe et al. (1994) Cell 78:681–692.
Loetscher et al. (1990) Cell 61, 351.
Tartaglia et al. (1993) Cell 74:845–853.
Itoh et al. (1991) Cell 66, 233–243.
Itoh et al. (1993) J Biol Chem 258, 10932.
Smith et al. (1994) Cell 76:959–962.
Schall et al. (1990) Cell 61, 361.

*Primary Examiner*—John Ulm
*Attorney, Agent, or Firm*—Flehr, Hohbach, Test, Albritton & Herbert

[57] ABSTRACT

A novel family of intracellular signaling proteins, exemplified by a Tumor Necrosis Factor Receptor-1 Associated Death Domain protein (TRADD), share a common TRADD sequence and include transducers of signals that modulate cell growth, differentiation and apoptosis. As such, the TRADD proteins, TRADD-encoding nucleic acids, and natural TRADD intracellular binding targets provide both important targets and means for therapeutic intervention. In particular, the invention provides isolated TRADDs and TRADD fragments, nucleic acids encoding the subject TRADDs and TRADD fragments or capable of selectively hybridizing to such TRADD-encoding nucleic acids, vectors and cells comprising TRADD-encoding nucleic acids, and TRADD-specific binding reagents. These compositions find use in diagnostic and therapeutic methods for disease associated with undesirable cell growth, migration, differentiation and/or cytokine signal responsiveness and methods and compositions for identifying lead compounds and pharmacological agents.

10 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 1441 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 49..984

( x i ) SEQUENCE DESCRIPTION: SEQ ID NO:1:

```
CTGGCGGGCG TGGGAACCCA GGCCCCGCCG AGGCGGCCAG GAGGTGAG ATG GCA GCT       57
                                                      Met Ala Ala
                                                        1

GGG CAA AAT GGG CAC GAA GAG TGG GTG GGC AGC GCA TAC CTG TTT GTG       105
Gly Gln Asn Gly His Glu Glu Trp Val Gly Ser Ala Tyr Leu Phe Val
        5              10                  15

GAG TCC TCG CTG GAC AAG GTG GTC CTG TCG GAT GCC TAC GCG CAC CCC       153
Glu Ser Ser Leu Asp Lys Val Val Leu Ser Asp Ala Tyr Ala His Pro
 20              25                  30                  35

CAG CAG AAG GTG GCA GTG TAC AGG GCT CTG CAG GCT GCC TTG GCA GAG       201
Gln Gln Lys Val Ala Val Tyr Arg Ala Leu Gln Ala Ala Leu Ala Glu
         40                  45                  50

AGC GGC GGG AGC CCG GAC GTG CTG CAG ATG CTG AAG ATC CAC CGC AGC       249
```

-continued

```
Ser Gly Gly Ser Pro Asp Val Leu Gln Met Leu Lys Ile His Arg Ser
             55                  60                  65

GAC CCG CAG CTG ATC GTG CAG CTG CGA TTC TGC GGG CGG CAG CCC TGT     297
Asp Pro Gln Leu Ile Val Gln Leu Arg Phe Cys Gly Arg Gln Pro Cys
         70                  75                  80

GGC CGC TTC CTC CGC GCC TAC CGC GAG GGG GCG CTG CGC GCC GCG CTG     345
Gly Arg Phe Leu Arg Ala Tyr Arg Glu Gly Ala Leu Arg Ala Ala Leu
     85                  90                  95

CAG AGG AGC CTG GCG GCC GCG CTC GCC CAG CAC TCG GTG CCG CTG CAA     393
Gln Arg Ser Leu Ala Ala Ala Leu Ala Gln His Ser Val Pro Leu Gln
100                 105                 110                 115

CTG GAG CTG CGC GCC GGC GCC GAG CGG CTG GAC GCT TTG CTG GCG GAC     441
Leu Glu Leu Arg Ala Gly Ala Glu Arg Leu Asp Ala Leu Leu Ala Asp
                120                 125                 130

GAG GAG CGC TGT TTG AGT TGC ATC CTA GCC CAG CAG CCC GAC CGG CTC     489
Glu Glu Arg Cys Leu Ser Cys Ile Leu Ala Gln Gln Pro Asp Arg Leu
            135                 140                 145

CGG GAT GAA GAA CTG GCT GAG CTG GAG GAT GCG CTG CGA AAT CTG AAG     537
Arg Asp Glu Glu Leu Ala Glu Leu Glu Asp Ala Leu Arg Asn Leu Lys
        150                 155                 160

TGC GGC TCG GGG GCC CGG GGT GGC GAC GGG GAG GTC GCT TCG GCC CCC     585
Cys Gly Ser Gly Ala Arg Gly Gly Asp Gly Glu Val Ala Ser Ala Pro
    165                 170                 175

TTG CAG CCC CCG GTG CCC TCT CTG TCG GAG GTG AAG CCG CCG CCG CCG     633
Leu Gln Pro Pro Val Pro Ser Leu Ser Glu Val Lys Pro Pro Pro Pro
180                 185                 190                 195

CCG CCA CCT GCC CAG ACT TTT CTG TTC CAG GGT CAG CCT GTA GTG AAT     681
Pro Pro Pro Ala Gln Thr Phe Leu Phe Gln Gly Gln Pro Val Val Asn
                200                 205                 210

CGG CCG CTG AGC CTG AAG GAC CAA CAG ACG TTC GCG CGC TCT GTG GGT     729
Arg Pro Leu Ser Leu Lys Asp Gln Gln Thr Phe Ala Arg Ser Val Gly
            215                 220                 225

CTC AAA TGG CGC AAG GTG GGG CGC TCA CTG CAG CGA GGC TGC CGG GCG     777
Leu Lys Trp Arg Lys Val Gly Arg Ser Leu Gln Arg Gly Cys Arg Ala
        230                 235                 240

CTG CGG GAC CCG GCG CTG GAC TCG CTG GCC TAC GAG TAC GAG CGC GAG     825
Leu Arg Asp Pro Ala Leu Asp Ser Leu Ala Tyr Glu Tyr Glu Arg Glu
    245                 250                 255

GGA CTG TAC GAG CAG GCC TTC CAG CTG CTG CGG CGC TTC GTG CAG GCC     873
Gly Leu Tyr Glu Gln Ala Phe Gln Leu Leu Arg Arg Phe Val Gln Ala
260                 265                 270                 275

GAG GGC CGC CGC GCC ACG CTG CAG CGC CTG GTG GAG GCA CTC GAG GAG     921
Glu Gly Arg Arg Ala Thr Leu Gln Arg Leu Val Glu Ala Leu Glu Glu
                280                 285                 290

AAC GAG CTC ACC AGC CTG GCA GAG GAC TTG CTG GGC CTG ACC GAT CCC     969
Asn Glu Leu Thr Ser Leu Ala Glu Asp Leu Leu Gly Leu Thr Asp Pro
            295                 300                 305

AAT GGC GGC CTG GCC TAGACCAGGG GTGCAGCCAG CTTTTGGAGA ACCTGGATGG    1024
Asn Gly Gly Leu Ala
            310

CCTTAGGGTT CCTTCTGCGG CTATTGCTGA ACCCCTGTCC ATCCACGGGA CCCTGAAACT  1084

CCACTTGGCC TATCTGCTGG ACCTGCTGGG GCAGAGTTGA TTGCCTTCCC CAGGAGCCAG  1144

ACCACTGGGG GTGCATCATT GGGGATTCTG CCTCAGGTAC TTTGATAGAG TGTGGGGTGG  1204

GGGGGACTTG CTTTGGAGAT CAGCCTCACC TTCTCCCATC CCAGAAGCGG GGCTTACAGC  1264

CAGCCCTTAC AGTTTCACTC ATGAAGCACC TTGATCTTTG GTGTCCTGGA CTTCATCCTG  1324

GGTGCTGCAG ATACTGCAGT GAAGTAAAAC AGGAATCAAT CTTGCCTGCC CCCAGCTCAC  1384

ACTCAGCGTG GGACCCCGAA TGTTAAGCAA TGATAATAAA GTATAACACG GAAAAAA    1441
```

( 2 ) INFORMATION FOR SEQ ID NO:2:

( i ) SEQUENCE CHARACTERISTICS:
    ( A ) LENGTH: 312 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Ala Ala Gly Gln Asn Gly His Glu Glu Trp Val Gly Ser Ala Tyr
 1               5                  10                  15

Leu Phe Val Glu Ser Ser Leu Asp Lys Val Val Leu Ser Asp Ala Tyr
            20                  25                  30

Ala His Pro Gln Gln Lys Val Ala Val Tyr Arg Ala Leu Gln Ala Ala
        35                  40                  45

Leu Ala Glu Ser Gly Gly Ser Pro Asp Val Leu Gln Met Leu Lys Ile
    50                  55                  60

His Arg Ser Asp Pro Gln Leu Ile Val Gln Leu Arg Phe Cys Gly Arg
65                  70                  75                  80

Gln Pro Cys Gly Arg Phe Leu Arg Ala Tyr Arg Glu Gly Ala Leu Arg
                85                  90                  95

Ala Ala Leu Gln Arg Ser Leu Ala Ala Ala Leu Ala Gln His Ser Val
            100                 105                 110

Pro Leu Gln Leu Glu Leu Arg Ala Gly Ala Glu Arg Leu Asp Ala Leu
            115                 120                 125

Leu Ala Asp Glu Glu Arg Cys Leu Ser Cys Ile Leu Ala Gln Gln Pro
    130                 135                 140

Asp Arg Leu Arg Asp Glu Glu Leu Ala Glu Leu Glu Asp Ala Leu Arg
145                 150                 155                 160

Asn Leu Lys Cys Gly Ser Gly Ala Arg Gly Gly Asp Gly Glu Val Ala
                165                 170                 175

Ser Ala Pro Leu Gln Pro Pro Val Pro Ser Leu Ser Glu Val Lys Pro
            180                 185                 190

Pro Pro Pro Pro Pro Pro Ala Gln Thr Phe Leu Phe Gln Gly Gln Pro
            195                 200                 205

Val Val Asn Arg Pro Leu Ser Leu Lys Asp Gln Gln Thr Phe Ala Arg
    210                 215                 220

Ser Val Gly Leu Lys Trp Arg Lys Val Gly Arg Ser Leu Gln Arg Gly
225                 230                 235                 240

Cys Arg Ala Leu Arg Asp Pro Ala Leu Asp Ser Leu Ala Tyr Glu Tyr
                245                 250                 255

Glu Arg Glu Gly Leu Tyr Glu Gln Ala Phe Gln Leu Leu Arg Arg Phe
            260                 265                 270

Val Gln Ala Glu Gly Arg Arg Ala Thr Leu Gln Arg Leu Val Glu Ala
            275                 280                 285

Leu Glu Glu Asn Glu Leu Thr Ser Leu Ala Glu Asp Leu Leu Gly Leu
    290                 295                 300

Thr Asp Pro Asn Gly Gly Leu Ala
305                 310
```

( 2 ) INFORMATION FOR SEQ ID NO:3:

( i ) SEQUENCE CHARACTERISTICS:
    ( A ) LENGTH: 1384 base pairs
    ( B ) TYPE: nucleic acid
    ( C ) STRANDEDNESS: double ( D ) TOPOLOGY: linear ( i i ) MOLECULE TYPE: cDNA ( i x ) FEATURE:
    ( A ) NAME/KEY: CDS
    ( B ) LOCATION: 1..681

( i x ) FEATURE:
    ( A ) NAME/KEY: mat_peptide
    ( B ) LOCATION: 1..681

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| GGC | TTC | CTC | CAA | GCC | TAC | CGC | GAG | GGG | GCG | CTG | CGC | ACC | GCG | CTG | CAG | 48 |
| Gly | Phe | Leu | Gln | Ala | Tyr | Arg | Glu | Gly | Ala | Leu | Arg | Thr | Ala | Leu | Gln | |
| 1 | | | | 5 | | | | | 10 | | | | | 15 | | |
| AGG | TGC | ATG | GCC | CCG | GCG | CTT | GCC | CAG | GAA | GCG | CTG | CGG | TTG | CAG | CTG | 96 |
| Arg | Cys | Met | Ala | Pro | Ala | Leu | Ala | Gln | Glu | Ala | Leu | Arg | Leu | Gln | Leu | |
| | | | 20 | | | | | 25 | | | | | 30 | | | |
| GAG | TTG | CGT | GCA | GGT | GCG | GAG | CAG | CTG | GAC | AGT | TGG | CTG | ACT | GAT | GAA | 144 |
| Glu | Leu | Arg | Ala | Gly | Ala | Glu | Gln | Leu | Asp | Ser | Trp | Leu | Thr | Asp | Glu | |
| | | 35 | | | | | 40 | | | | | 45 | | | | |
| GAG | CGC | TGT | TTG | AAT | TAC | ATC | TTA | GCC | CAG | AAG | CCC | GAC | CGG | CTC | AGG | 192 |
| Glu | Arg | Cys | Leu | Asn | Tyr | Ile | Leu | Ala | Gln | Lys | Pro | Asp | Arg | Leu | Arg | |
| | 50 | | | | | 55 | | | | | 60 | | | | | |
| GAC | GAG | GAA | CTC | GCG | GAG | CTG | GAG | GAT | GAG | CTC | TGC | AAA | CTG | ACG | TGT | 240 |
| Asp | Glu | Glu | Leu | Ala | Glu | Leu | Glu | Asp | Glu | Leu | Cys | Lys | Leu | Thr | Cys | |
| 65 | | | | | 70 | | | | | 75 | | | | | 80 | |
| GAC | TGC | ACT | GGC | CAG | GGT | GGA | GCC | ATA | CAG | GTA | GCT | TCT | GCA | GGT | TCG | 288 |
| Asp | Cys | Thr | Gly | Gln | Gly | Gly | Ala | Ile | Gln | Val | Ala | Ser | Ala | Gly | Ser | |
| | | | | 85 | | | | | 90 | | | | | 95 | | |
| AAG | TTC | CCG | GTT | TCC | TCT | CCG | ACC | GAG | GAG | AAA | CCA | CTG | CCG | GCC | GCC | 336 |
| Lys | Phe | Pro | Val | Ser | Ser | Pro | Thr | Glu | Glu | Lys | Pro | Leu | Pro | Ala | Ala | |
| | | | 100 | | | | | 105 | | | | | 110 | | | |
| TGC | CAG | ACT | TTT | CTG | TTC | CAC | GGG | CAG | CTC | GTA | GTG | AAC | CGG | CCA | CTG | 384 |
| Cys | Gln | Thr | Phe | Leu | Phe | His | Gly | Gln | Leu | Val | Val | Asn | Arg | Pro | Leu | |
| | | 115 | | | | | 120 | | | | | 125 | | | | |
| ACT | CTT | CAA | GAC | CAG | CAG | ACG | TTT | GCG | CGC | TCG | GTG | GGT | CTC | AAG | TGG | 432 |
| Thr | Leu | Gln | Asp | Gln | Gln | Thr | Phe | Ala | Arg | Ser | Val | Gly | Leu | Lys | Trp | |
| | 130 | | | | | 135 | | | | | 140 | | | | | |
| CGC | AGG | GTG | GGG | CGC | TCG | CTG | CAG | CGT | AAC | TGT | CGG | GCA | CTG | AGA | GAT | 480 |
| Arg | Arg | Val | Gly | Arg | Ser | Leu | Gln | Arg | Asn | Cys | Arg | Ala | Leu | Arg | Asp | |
| 145 | | | | | 150 | | | | | 155 | | | | | 160 | |
| CCT | GCC | CTC | GAC | TCG | CTG | GCC | TAC | GAG | TAT | GAG | CGT | GAT | GGG | CTA | TAC | 528 |
| Pro | Ala | Leu | Asp | Ser | Leu | Ala | Tyr | Glu | Tyr | Glu | Arg | Asp | Gly | Leu | Tyr | |
| | | | | 165 | | | | | 170 | | | | | 175 | | |
| GAG | CAG | GCC | TTC | CAG | CTG | CTG | CGC | CGT | TTC | ATG | CAA | GCC | GAG | GGC | CGC | 576 |
| Glu | Gln | Ala | Phe | Gln | Leu | Leu | Arg | Arg | Phe | Met | Gln | Ala | Glu | Gly | Arg | |
| | | | 180 | | | | | 185 | | | | | 190 | | | |
| CGT | GCC | ACA | CTG | CAG | CGC | CTG | GTG | GAG | GCG | CTG | GAG | GAG | AAC | GAA | CTC | 624 |
| Arg | Ala | Thr | Leu | Gln | Arg | Leu | Val | Glu | Ala | Leu | Glu | Glu | Asn | Glu | Leu | |
| | | 195 | | | | | 200 | | | | | 205 | | | | |
| ACT | AGT | CTA | GCA | GGA | GGG | ATC | TTG | TTG | GGC | CAG | GCG | GAG | CCG | GAT | GGC | 672 |
| Thr | Ser | Leu | Ala | Gly | Gly | Ile | Leu | Leu | Gly | Gln | Ala | Glu | Pro | Asp | Gly | |
| | 210 | | | | | 215 | | | | | 220 | | | | | |

| | | | | |
|---|---|---|---|---|
| GGC | CTG | GCC | TAAGTCTAGT ACTGTGGGGA AGGGCGGCCA ACCAGCAGTT | 721 |
| Gly | Leu | Ala | | |
| 225 | | | | |

| | | | | |
|---|---|---|---|---|
| CAGTGTTTGA | AACCCACGGG | TGGCTGTTGG | GGTATTTTTT ACCGCTGATG TTGTACTGTT | 781 |
| GACCACTTTC | CATCTACTGG | ACTTGGAGAG | CATACGCACG CCCCACCTAG CTGAGCTGCT | 841 |
| GGAGTGCAAC | TAACTGCCCC | TCCCCCCGCC | CCCCAGGAGT CAGGCAAGCA GCGCAGGGGT | 901 |

| | | | | |
|---|---|---|---|---|
| AAATCACTGA | TGATCATACA | AAAAGAGGAC | TTGCTGCAAA | GACCCTCTAA | GTACCCGGAC | 961 |
| CTTCTGAAAC | CTAGTCAAGG | TGCTACAAAA | ACTGTCGGGA | GCAGGATGAC | GATTTTCCCC | 1021 |
| GCCCTTGGAT | ATACTCATCG | TGGGACCGAA | GCACCTTGTC | TGAGCGATAA | TAAAATGTAA | 1081 |
| CTCTTTTACA | GACTTGCGGA | GATGCTGAGG | TCTAGACCTG | GTTGGGGTTA | GTCACCTCAG | 1141 |
| TGGAATAGTG | AGCCAGGTAG | AGTAGGGAGT | GGAGAGACAG | GCAGGGTTCG | GGTAGGGCCT | 1201 |
| TGAGGAAGGT | GAGAGGAAGG | GGTTGCTACC | TGTCCTGTTA | GTGAAGGATA | ACCGGGGGTT | 1261 |
| TGGTGAACCA | TCATTACATT | AGGTTTGGTT | TTGTTTGGTG | TGTGTATCTA | AGTATTGTGC | 1321 |
| TTTAAAACAT | CTACCGTGTC | CTGAATTAGA | AAATTAAAAT | TTCAGCCAGA | AAAAAAAAAA | 1381 |
| AAA | | | | | | 1384 |

( 2 ) INFORMATION FOR SEQ ID NO:4:

( i ) SEQUENCE CHARACTERISTICS:
        ( A ) LENGTH: 227 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Gly Phe Leu Gln Ala Tyr Arg Glu Gly Ala Leu Arg Thr Ala Leu Gln
  1               5                  10                  15
Arg Cys Met Ala Pro Ala Leu Ala Gln Glu Ala Leu Arg Leu Gln Leu
                 20                  25                  30
Glu Leu Arg Ala Gly Ala Glu Gln Leu Asp Ser Trp Leu Thr Asp Glu
             35                  40                  45
Glu Arg Cys Leu Asn Tyr Ile Leu Ala Gln Lys Pro Asp Arg Leu Arg
         50                  55                  60
Asp Glu Glu Leu Ala Leu Glu Asp Glu Leu Cys Lys Leu Thr Cys
 65                  70                  75                  80
Asp Cys Thr Gly Gln Gly Gly Ala Ile Gln Val Ala Ser Ala Gly Ser
                 85                  90                  95
Lys Phe Pro Val Ser Ser Pro Thr Glu Glu Lys Pro Leu Pro Ala Ala
                100                 105                 110
Cys Gln Thr Phe Leu Phe His Gly Gln Leu Val Val Asn Arg Pro Leu
                115                 120                 125
Thr Leu Gln Asp Gln Gln Thr Phe Ala Arg Ser Val Gly Leu Lys Trp
        130                 135                 140
Arg Arg Val Gly Arg Ser Leu Gln Arg Asn Cys Arg Ala Leu Arg Asp
145                 150                 155                 160
Pro Ala Leu Asp Ser Leu Ala Tyr Glu Tyr Glu Arg Asp Gly Leu Tyr
                165                 170                 175
Glu Gln Ala Phe Gln Leu Leu Arg Arg Phe Met Gln Ala Glu Gly Arg
                180                 185                 190
Arg Ala Thr Leu Gln Arg Leu Val Glu Ala Leu Glu Glu Asn Glu Leu
                195                 200                 205
Thr Ser Leu Ala Gly Gly Ile Leu Leu Gly Gln Ala Glu Pro Asp Gly
        210                 215                 220
Gly Leu Ala
225
```

( 2 ) INFORMATION FOR SEQ ID NO:5:

( i ) SEQUENCE CHARACTERISTICS:
        ( A ) LENGTH: 14 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Met Ala Ser Met Glu Gln Lys Leu Ile Ser Glu Glu Asp Leu
1               5                   10

TNF RECEPTOR-ASSOCIATED INTRACELLULAR SIGNALING PROTEINS AND METHODS OF USE

INTRODUCTION

1. Field of the Invention

The field of this invention is human intracellular death domain-containing signaling proteins.

2. Background

Tumor necrosis factor (TNF) is a cytokine produced mainly by activated macrophages. Two distinct TNF receptors of 55 kd (TNF-R1) and 75 kd (TNF-R2) have been identified. These TNF receptors are members of the larger TNF receptor superfamily which also includes the Fas antigen, CD27, CD30, CD40, and the low affinity nerve growth factor receptor. TNF-R1 is responsible for most of TNF's biological properties, including programmed cell death, antiviral activity and activation of the transcription factor NF-kB in a wide variety of cell types. It also plays an essential role in host defense against microorganisms and bacterial pathogens. Mutagenesis studies have identified a "death domain" of approximately 80 amino acids near the C-terminus of TNF-R1 that is required for signaling antiviral activity and cell death. The death domain of TNF-R1 probably also triggers activation of an endosomal acidic sphingomyelinase (A-SMase). A homologous domain, that can also initiate programmed cell death, is found in the Fas antigen. The apoptosis induced by both TNF and Fas was recently shown to involve the activation of the interleukin-1$b$ converting enzyme (ICE) or an ICE-like cysteine protease (Tewari and Dixit, 1995). ICE is related in primary amino acid sequence to the ced-3 gene product which plays an essential role in programmed cell death in C. elegans. ICE has been predicted to be involved in mammalian programmed cell death (Yuan et at., 1993).

Identifying and developing new pharmaceuticals is a multibillion dollar industry in the U.S. Urgently needed are efficient methods of identifying pharmacological agents which, if amenable to automated, cost-effective, high throughput drug screening, would have immediate application in a broad range of domestic and international pharmaceutical and biotechnology drug development programs. As TNF is involved in the signaling of a number of cellular responses including cytotoxicity, anti-viral activity, immuno-regulatory activities and the transcriptional regulation of a number of genes, it is desired to identify agents which specifically modulate transduction of TNF signaling. Unfortunately, the TNF-R1-associated proteins involved in generating the various TNF-induced signals remain unknown; hence, the reagents necessary for the development of high-throughput screening assays for such therapeutics are unavailable.

RELEVANT LITERATURE

VanArsdale and Ware (1994) J Immunology 153:3043–3050 describe proteins associated with TNF-R1. Rothe et al. (1994) Cell 78:681–692 report the identification of a family of putative signal transducers associated with the cytoplasmic domain of the 75 kD TNF-R2. The cloning and amino acid sequencing of TNF-R1 is disclosed in Schall et al (1990) Cell 61,361 and Loetscher et al (1990) Cell 61,351; the identification of a "death domain" in TNF-R1 is disclosed in Tartaglia et al. (1993) Cell 74:845–853. The cloning and amino acid sequencing of the Fas antigen is disclosed in Itoh et al (1991) Cell 66, 233–243; a mutational analysis of the Fas antigen is described in Itoh et at. (1993) J Biol Chem 268, 10932. For a recent review, see Smith et al. (1994) Cell 76:959–962.

SUMMARY OF THE INVENTION

The invention provides methods and compositions relating to a novel family of intracellular signaling proteins exemplified by a Tumor necrosis factor Receptor-1 Associated Death Domain protein (TRADD). The subject proteins share common TRADD sequences and include transducers of signals that modulate cell growth, differentiation and apoptosis. As such, the subject TRADD proteins, TRADD-encoding nucleic acids, and natural TRADD intracellular binding targets provide both important targets and means for therapeutic intervention. In particular, the invention provides isolated TRADDs and TRADD fragments, nucleic acids encoding the subject TRADDs and TRADD fragments or capable of selectively hybridizing to such TRADD-encoding nucleic acids, vectors and cells comprising TRADD-encoding nucleic acids, and TRADD-specific binding reagents. The invention also provides diagnostic and therapeutic methods and compositions for disease associated with undesirable cell growth, migration, differentiation and/or cytokine signal responsiveness and methods and compositions for identifying lead compounds and pharmacological agents.

DETAILED DESCRIPTION OF THE INVENTION

The invention provides methods and compositions relating to a novel family of intracellular signaling proteins comprising a TRADD or TRADD fragment, especially a TRADD Death Domain. The subject proteins include transducers and effectors of signals that modulate cellular function involving gene transcription, cell growth, differentiation, migration and apoptosis. In particular, TNF signaling is involved in tumoricidal activity, anti-infection activity (e.g. host immune responsiveness to pathogenic infections of HIV, *Helicobacter pylori, Myobacterium tuberculosis*, etc.), cachexia associated with chronic disease, cartilage destruction (e.g. in rheumatoid arthritis), immune cell recruitment, sepsis and septic shock (e.g. adult respiratory distress syndrome), vascular disease (e.g. atherosclerosis), diabetes mellitus type I, multiple sclerosis, gastritis, etc.

The subject TRADD fragments have one or more TRADD-specific binding affinities, such as the ability to specifically bind at least one natural intracellular TRADD-specific binding target or a TRADD-specific binding agent such as a TRADD-specific antibody or a TRADD-specific binding agent identified in assays such as described below. Preferred TRADD fragments are capable of at least one of specifically binding another TRADD (oligomerizing), specifically binding TNF-R1, transducing TNF-R1 signaling, activating TRADD-specific transcription, activating TRADD-specific apoptsis, or inhibiting any of the foregoing functions, or eliciting an antibody capable of specifically binding a TRADD.

Methods for making immunogenic peptides through the use of conjugates, adjuvants, etc. and methods for eliciting antibodies, e.g. immunizing rabbits, are well known. Convenient ways to verify the ability of a given TRADD fragment to specifically bind such targets include in vitro labelled binding assays such as described below. The specificity of TRADD fragment specific binding agents may be confirmed by ensuring non-cross-reactivity with non- TRADD related proteins and protein fragments such as TNF-R1 and Fas antigen death domains. Other natural TRADD binding targets are readily identified by screening cells, membranes and cellular extracts and fractions with the disclosed materials and methods and by other methods known in the art. For example, two-hybrid screening using TRADD fragments are used to identify intracellular targets which specifically bind such fragments.

The subject TRADD fragments maintain binding affinity of not less than three, preferably not less than two, more preferably not less than one order of magnitude less than the binding equilibrium constant of the corresponding full-length native TRADD to the binding target under similar conditions. Particular TRADD fragments or deletion mutants are shown to function in a dominant-negative fashion. Such fragments provide therapeutic agents, e.g. when delivered by intracellular immunization—transfection of susceptible cells with nucleic acids encoding such mutants.

The subject TRADD fragments are of length sufficient to provide a novel peptide: such peptides are at least 6, usually at least about 7, more usually at least about 8, most usually at least about 10 amino acids. The claimed TRADD and fragments thereof are isolated, partially pure or pure and are typically recombinantly produced. An "isolated" peptide is unaccompanied by at least some of the material with which it is associated in its natural state and constitutes at least about 0.5%, preferably at least about 2%, and more preferably at least about 5% by weight of the total protein (including peptide fragments) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample. The TRADD fragments may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc.

Preferred TRADD fragments derive at least in part from the TRADD death domain region. Particularly preferred TRADD death domain fragments comprise one or more conserved TRADD death domain peptides include from the N-terminal end of the Death Domain, VVNRPL (SEQUENCE ID NO:2, residues 209–214), DQQTRAR (SEQUENCE ID NO:2, residues 218–224), SVGLKWR (SEQUENCE ID NO:2, residues 225–231), VGRSLQR (SEQUENCE ID NO:2, residues 233–239), CRALRD (SEQUENCE ID NO:2, residues 241–246), PALDSL (SEQUENCE ID NO:2, residues 247–252), AYEYER (SEQUENCE ID NO:2, residues 253–258), GLYEQA (SEQUENCE ID NO:2, residues 260–265), FQLLRRF (SEQUENCE ID NO:2, residues 266–272), QAEGRRA (SEQUENCE ID NO:2, residues 274–280), TLQRLV (SEQUENCE ID NO:2, residues 281–286), EALEEN (SEQUENCE ID NO:2, residues 287–292) and ELTSLA (SEQUENCE ID NO:2, residues 293–298).

A wide variety of molecular and biochemical methods are available for generating and expressing TRADD fragments, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. For example, TRADD or fragments thereof may be obtained by chemical synthesis, expression in bacteria such as $E.$ $coli$ and eukaryotes such as yeast, baculovirus, or mammalian cell-based expression systems, etc., depending on the size, nature and quantity of the TRADD or fragment.

The invention provides TRADD-specific binding agents, methods of identifying and making such agents, and their use in diagnosis, therapy and pharmaceutical development. For example, TRADD-specific agents are useful in a variety of diagnostic and therapeutic applications, especially where disease or disease prognosis is associated with improper utilization of a pathway involving TRADD, e.g. TNFR1 activation, TNF expression, etc. Novel TRADD-specific binding agents include TRADD-specific antibodies and other natural intracellular binding agents identified with assays such as one- and two-hybrid screens, non-natural intracellular binding agents identified in screens of chemical libraries, etc.

Generally, TRADD-specificity of the binding target is shown by binding equilibrium constants. Such targets are capable of selectively binding a TRADD, i.e. with an equilibrium constant at least about $10^7$ $M^{-1}$, preferably at least about $10^8 M^{-1}$, more preferably at least about $10^9$–1. A wide variety of cell-based and cell-free assays may be used to demonstrate TRADD-specific binding. Cell based assays include one, two and three-hybrid screens, mediating or competitively inhibiting TRADD-mediated transcription, etc. Preferred are rapid in vitro, cell-free assays such as mediating or inhibiting TRADD-protein (e.g. TRADD-TNF-R1 death domain), immunoassays, etc. Other useful screening assays for TRADD/TRADD fragment-target binding include fluorescence resonance energy transfer (FRET), electrophoretic mobility shift analysis (EMSA), etc.

The invention also provides nucleic acids encoding the subject TRADD and fragments, which nucleic acids may be part of TRADD-expression vectors and may be incorporated into recombinant cells for expression and screening, transgenic animals for functional studies (e.g. the efficacy of candidate drugs for disease associated with expression of a TRADD), etc. Nucleic acids encoding TRADD containing proteins are isolated from eukaryotic cells, preferably human cells, by screening cDNA libraries with probes or PCR primers derived from the disclosed TRADD cDNAs. In addition, the invention provides nucleic acids sharing sufficient sequence similarity with that of one or more disclosed TRADD-encoding nucleic acids or fragment thereof to effect hybridization. Such substantially identical or homologous nucleic acids are capable of hybridizing to the TRADD-encoding nucleic acid defined by SEQUENCE ID NO: 1 or 3 under stringency conditions characterized by a hybridization buffer comprising 0% formamide in 0.9M saline/0.09M sodium citrate (SSC) buffer at a temperature of 37° C. and remaining bound when subject to washing at 42° C. with the SSC buffer at 37° C. Preferred nucleic acids will hybridize in a hybridization buffer comprising 20% formamide in 0.9M saline/0.09M sodium citrate (SSC) buffer at a temperature of 42° C. and remaining bound when subject to washing at 42° C. with 2 X SSC buffer at 42° C. More preferred nucleic acids encode invariant TRADD sequences and a TRADD with 50% pair-wise identity to that of SEQUENCE ID NO:2.

The subject nucleic acids are isolated, meaning they comprise a sequence joined to a nucleotide other than that which it is joined to on a natural chromosome and usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The subject nucleic acids find a wide variety of applications including use as translatable transcripts, hybridization probes, PCR primers, therapeutic nucleic acids, etc.; use in detecting the presence of TRADD Death Domain genes and gene transcripts, in detecting or amplifying nucleic acids encoding additional TRADD Death Domain homologs and structural analogs, and in gene therapy applications.

For example, therapeutic TRADD nucleic acids are used to modulate cellular expression or intracellular concentration or availability of active TRADD. In particular, where cell-specific apoptosis or other limitation of cell growth is desired, e.g. neoproliferative disease, cytostatic TRADD Death Domain encoding nucleic acids are introduced into the targeted cell type. A wide variety of neoproliferative indications may be treated, either prophylactically or therapeutically with the subject compositions. Conditions for treatment include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection where endothelial cells are involved, infectious diseases such as HIV infection where certain immune cells and other infected cells are involved, or the like.

In other situations where it is desired to reduce cytokine, particularly TNF, responsiveness, nucleic acids capable of inhibiting translation of a TRADD or TRADD fragment containing protein are introduced. These nucleic acids are typically antisense: single-stranded sequences comprising complements of the disclosed relevant TRADD fragment-encoding nucleic acid. Antisense modulation of the expression of a given TRADD fragment containing protein may employ TRADD fragment antisense nucleic acids operably linked to gene regulatory sequences. Cell are transfected with a vector comprising a TRADD fragment sequence with a promoter sequence oriented such that transcription of the gene yields an antisense transcript capable of binding to endogenous TRADD fragment containing protein encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given TRADD fragment containing protein may be administered to the target cell, in or temporarily isolated from a host, at a concentration that results in a substantial reduction in expression of the targeted protein.

Various techniques may be employed for introducing of the nucleic acids into viable cells. The techniques vary depending upon whether one is using the subject compositions in culture or in vivo in a host. Various techniques which have been found efficient include transfection with a retrovirus, viral coat protein-liposome mediated transfection, see Dzau et at., *Trends in Biotech* 11,205–210 (1993). In some situations it is desirable to provide the nucleic acid source with an agent which targets the target cells, such as an antibody specific for a surface membrane protein on the target cell, a ligand for a receptor on the target cell, etc. Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. In liposomes, the decoy concentration in the lumen will generally be in the range of about 0.1 µM to 20 µM. For other techniques, the application rate is determined empirically, using conventional techniques to determine desired ranges.

Usually, application of the subject therapeutics will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. Systemic administration of the nucleic acid using lipofection, liposomes with tissue targeting (e.g. antibody) may also be employed.

The invention provides efficient methods of identifying pharmacological agents or lead compounds for agents active at the level of a TRADD or TRADD fragment modulatable cellular function, particularly a TRADD Death Domain mediated signal transduction, especially apoptosis. Generally, these screening methods involve assaying for compounds which interfere with a TRADD activity such as a TRADD Death Domain-TNF-R1 binding, etc. The methods are amenable to automated, cost-effective high throughput drug screening and have immediate application in a broad range of domestic and international pharmaceutical and biotechnology drug development programs. Target therapeutic indications are limited only in that the target cellular function be subject to modulation, usually inhibition, by disruption of the formation of a complex comprising a TRADD fragment and one or more natural TRADD fragment intracellular binding targets. Target indications may include infection, genetic disease, cell growth and regulatory disfunction, such as neoplasia, inflammation, hypersensitivity, etc and other indication discussed herein.

A wide variety of assays for binding agents are provided including labelled in vitro protein-protein binding assays, electrophoretic mobility shift assays, immunoassays, cell based assays such as one, two and three hybrid screens, expression assays, etc. For example, three-hybrid screens are used to rapidly examine the effect of transfected nucleic acids, which may, for example, encode combinatorial peptide libraries or antisense molecules, on the intracellular binding of TRADD fragments to specific intracellular targets. Convenient reagents for such assays (e.g. GAL4 fusion partners) are known in the art. An exemplary cell-based assay involves transfecting with a TRADD fragment a TNF-R1 expressing cell having a inducible reporter (e.g. gene encoding luciferase), the expression of which is operably linked to a gene expression regulatory region (e.g. NF-κB binding site) activated, at least indirectly, by the TRADD fragment. Agents which modulate TRADD fragment mediated cell function are then detected through a change in the reporter. Preferred methods are rapid, in vitro, protein binding assays.

TRADD fragments used the methods are usually added in an isolated, partially pure or pure form and are typically recombinantly produced. The TRADD or TRADD fragment may be part of a fusion product with another peptide or polypeptide, e.g. a polypeptide that is capable of providing or enhancing protein-protein binding, sequence-specific nucleic acid binding or stability under assay conditions (e.g. a tag for detection or anchoring).

The assay mixtures comprise at least a portion of a natural intracellular TRADD fragment binding target such as the C-terminus TNF-R1 death domain. Where the natural intracellular TRADD fragment binding targets includes a nucleic acid, the mixture may comprise a nucleic acid comprising a sequence which shares sufficient sequence similarity with a gene or gene regulatory region to which the native (wild-type) TRADD fragment naturally binds to provide sequence-specific binding of the fragment. Such a nucleic acid may further comprise one or more sequences which facilitate the binding of a second protein or fragment thereof which cooperatively binds the nucleic acid with the TRADD fragment (i.e. at least one increases the affinity or specificity of the DNA binding of the other). While native binding targets may be used, it is frequently preferred to use portions (e.g. peptides, nucleic acid fragments) or analogs (i.e. agents which mimic the TRADD Death Domain binding properties of the natural binding target for the purposes of the assay) thereof so long as the portion provides binding affinity and avidity to the subject TRADD fragment conveniently measurable in the assay.

The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, sterols, isoprenoids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the TRADD fragment specifically binds the cellular binding target, portion or analog. The mixture components can be added in any order that provides for the requisite bindings. Incubations may be performed at any temperature which facilitates optimal binding, typically between 4 and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the TRADD fragment and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. For cell based assays such as one, two, and three hybrid screens, the transcript resulting from TRADD fragment-target binding usually encodes a directly or indirectly detectable product (e.g. galactosidase activity, luciferase activity, etc.). For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening. Candidate agents shown to inhibit TRADD fragment—target binding provide valuable reagents to the biotechnology industries. In addition, the reagents find use in the pharmaceutical industries for animal and human trials; for example, the reagents may be derivatized and rescreened in in vitro and in vivo assays to optimize activity and minimize toxicity for pharmaceutical development.

As previously described, the methods are particularly suited to automated high throughput drug screening. In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microtiter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained-in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates. Of course, useful agents are identified with a range of other assays (e.g. gel shifts, etc.) employing the subject TRADD fragments.

The following experiments and examples are offered by way of illustration and not by way of limitation,

EXPERIMENTAL

Here we describe the molecular cloning of a human TRADD that interacts specifically with the death domain of TNF-R1. We show that over-expression of this TRADD activates two major TNF signaling pathways, apoptosis and NF-κB activation. Furthermore, the ICE inhibitor encoded by the cowpox virus crmA gene, which protects against apoptosis induced by TNF (Tewari and Dixit, 1995), also protects against TRADD-mediated cell death. However, crmA does not prevent TRADD-induced NF-κB activation, demonstrating that the two signaling pathways emanating from this TRADD are distinct.

Isolation of cDNA Clones Encoding TNF-R1-Interacting Proteins: To identify proteins that directly interact with the intracellular region of TNF-R1 we used the yeast two-hybrid system (Fields and Song, 1989). The yeast indicator strain HF7c was sequentially transformed with: i) an expression vector encoding the intracellular domain (amino acids 214–426) of human TNF-R1 fused to the yeast GAL4 DNA binding domain (GAL4bd-TNF-R1icd); and ii) GAL4 activation domain-tagged cDNA expression libraries prepared from HeLa and B cell mRNA. 48 positive clones, as determined by activation of his and lacZ reporter genes, were obtained from approximately 50 million transformants. 41 of these clones encoded portions of the cytoplasmic region of TNF-R1, indicating that the "death domain" (Tartaglia et al., 1993) of the receptor can self-associate. Similar findings using the yeast two-hybrid system were reported recently (Song et at., 1994; Boldin et al., 1995). DNA sequence analysis indicated that three [H10 (219aa), B27 (194aa), B36 (118aa)] of the remaining 7 clones were partial length cDNAs derived from the same gene. To isolate a full length cDNA we screened a human umbilical vein endothelial cell (HUVEC) cDNA library using the B27 cDNA as probe and obtained several cDNA clones of approximately 1.5 kb. DNA sequence analysis of these clones revealed an open reading frame (SEQUENCE ID NO: 1) predicted to encode a protein of 312 amino acids (SEQUENCE ID NO:2) with a molecular mass of 34.2 kDa that we have designated TNF-R1 Associated Death Domain protein or TRADD. Database searches utilizing BLAST and FASTA programs failed to identify any proteins having significant sequence similarity to TRADD. A murine TRADD cDNA and encoded Death Domain is disclosed in SEQUENCE ID NO:3 and 4, respectively.

TRADD mRNA is Ubiquitously Expressed: Northern blot analysis indicated that low amounts of TRADD mRNA were expressed constitutively in all human tissues examined. This result is consistent with TRADD involvement in TNF-R1 signal transduction as TNF-R1 mRNA is also expressed ubiquitously (Loetscher et al., 1990; Schall et at., 1990; Lewis et at., 1991). The 1.4 kb size of the TRADD transcript confirms that the cDNA clones isolated from the HUVEC cDNA library represent full length copies of TRADD mRNA.

Detection of Endogenous TRADD: We prepared polyclonal antibodies against TRADD in order to examine the endogenously expressed protein. These antibodies were generated by expressing TRADD in *E. coli* as a GST fusion protein and using the purified GST-TRADD chimera as immunogen. Rabbit anti-TRADD antiserum specifically recognized two proteins of approximately 34 kDa when tested by Western analysis using lysates prepared from 293 cells transiently transfected with a TRADD expression vector. The weak upper band of the doublet may be a post-translationally modified TRADD. Protein bands of the same size, corresponding to endogenous TRADD, could be detected in lysates from ECV304, HeLa, and HepG2 cells prepared using 50-fold more cells. These results indicate that the TRADD cDNA clone encodes a full length copy of the TRADD protein.

TRADD Specifically Interacts with TNF-R1 and Self-Associates: To confirm that full length TRADD interacts specifically with TNF-R1, several additional two-hybrid assays were performed. A protein consisting of the GAL4 activation domain fused to full length TRADD (GAL4ad-TRADD) was co-expressed with the GAL4bd-TNF-R1icd fusion protein in yeast strain SFY526. The GAL4ad-TRADD chimera interacted with the GAL4bd-TNF-R1icd fusion protein, but not with the GAL4 DNA binding domain alone. We also tested the ability of the GAL4ad-TRADD fusion protein to interact with receptors that are related to TNF-R1 either in terms of their structure (TNF-R2 and Fas antigen) or the signals they generate (Fas antigen and the type I IL-1 receptor [IL1-R1]). However, GAL4ad-TRADD failed to interact with the cytoplasmic domains of TNF-R2, IL1-R1, or Fas antigen expressed as GAL4bd chimeras.

To further examine the specificity of the interaction between TRADD and TNF-R1, the GAL4bd was fused to two different C-terminal deletion mutants of TNF-R1icd (Tartaglia et al., 1993b) as well as to the cytoplasmic domain of murine TNF-R1. GAL4ad-TRADD interacted strongly with an active receptor mutant (D413-426) lacking 14 amino acids, yet interacted weakly with an inactive mutant (D407-426) lacking 20 amino acids. These results indicate that amino acids 407-412 of TNF-R1, which are required for the signaling of cytotoxicity, antiviral activity (Tartaglia et al., 1993b) and NF-KB activation, contribute to, but are not required for its TRADD interaction. The interaction of TRADD with mouse TNF-R1 in this assay system was specific, but weaker than with the homologous human TNF-R1.

We next performed in vitro biochemical assays to confirm the specific interaction of TNF-R1 with TRADD observed in the two-hybrid system. GST fusion proteins containing the cytoplasmic domains of TNF-R1, TNF-R2, IL1-R1 and Fas antigen were expressed in E. coli and purified. These fusion proteins were tested for interaction with $^{35}$S-labeled TRADD prepared by in vitro transcription and translation. TRADD associated only with the GST-TNF-R1 fusion protein. Furthermore, TRADD did not associate with a GST-TNF-R1 (−20) fusion protein derived from the inactive TNF-R1 mutant D407-426.

To determine whether TRADD exists as a monomer we prepared a "reverse" two-hybrid construct in which TRADD was fused to the GAL4bd. The results of a yeast cotransformation experiment using this construct and the GAL4ad-TRADD construct indicated that these two hybrid proteins interact with each other. We conclude that TRADD is an oligomeric protein.

TRADD: TNF-R1 Interaction in Human Cells: Extensive mutational analysis of TNF-R1 has led to the identification of several residues in its "death" domain that are important for the generation: of a cytotoxic response (Tartaglia et al., 1993b). To determine whether a correlation exists between the ability of a TNF-R1 mutant to deliver a cytotoxic signal and to interact with TRADD, we utilized a mammalian cell co-immunoprecipitation assay. An expression vector that directs the synthesis of TRADD containing an N-terminal myc epitope tag was cotransfected with various TNF-R1 constructs into human embryonic kidney 293 cells. Cell extracts were immunoprecipitated using polyclonal antibodies against the extracellular domain of TNF-R1 and coprecipitating TRADD was detected by western blotting with an anti-myc monoclonal antibody. As determined by this assay, TRADD specifically associates with TNF-R1. Five different deletion and point mutants of TNF-R1 were also examined by this method. The two active mutants (D413-426 and D212-308) were able to coprecipitate TRADD, whereas two of the three inactive mutants (D212-340 and K343,F345, R347) failed to do so. The third inactive mutant (D407-426) coprecipitated TRADD weakly in some experiments and not at all in others. Accordingly, it appears that residues throughout the ~80 amino acid death domain of TNF-R1 are critical for TRADD interaction.

Overexpression of TRADD Induces Apoptosis: One of the major activities signaled by TNF through TNF-R1 is programmed cell death or apoptosis. To investigate a possible role for TRADD in TNF-mediated apoptosis, 293 cells were transiently transfected with a TRADD expression vector and examined by phase contrast microscopy 24 hours later. 293 cells that overexpressed TRADD had obvious morphological differences from those transfected with a control vector. The TRADD-expressing cells displayed the typical characteristics of adherent cells undergoing apoptosis (reviewed in Tomei and Cope, 1991). Shortly following transfection these cells became rounded, condensed (average diameter~15 mm) and began to detach from the dish. Cells transfected with a control vector remained flat with an average length of~40-50 mm.

One biochemical hallmark of apoptosis is the internucleosomal fragmentation of nuclear DNA which results in a distinct laddering pattern when analyzed by agarose gel electrophoresis (Tomei and Cope, 1991). We examined nuclear DNA from 293 cells transfected with either a contol vector or with the TRADD expression vector. DNA isolated from TRADD-expressing cells displayed a profile characteristic of apoptosis and closely resembled the DNA from untransfected 293 cells that were treated with TNF. A small amount of DNA fragmentation was also observed in the vector control which we attribute to the transfection procedure.

It was recently shown (Tewari and Dixit, 1995) that TNF-induced apoptosis can be inhibited by the ICE-specific serpin inhibitor encoded by the cowpox crmA gene (Ray et al., 1992). This led us to examine the effects of crmA protein and other known inhibitors of apoptosis (Bcl-2 and adenovirus 19K E1B proteins) on TRADD-induced cell death. The appearance of 293 cells cotransfected with expression vectors encoding both TRADD and crmA was indistinguishable from cells transfected with a control vector alone. Conversely, co-expression of either the Bcl-2 or E1B gene product did not counteract the apoptotic effect of TRADD expression on 293 cells. Furthermore, crmA co-expression also blocked the generation of TRADD-induced DNA laddering. These results are consistent with the interpretation that TRADD-induced apoptosis involves activation of ICE or a related protease.

To ensure that the induction of apoptosis by TRADD was not a peculiarity of 293 cells, we also examined the effects of TRADD overexpression on HeLa, HepG2, and murine NIH-3T3 cells. In these cases, low transient transfection efficiency precluded use of the assays described above for 293 cells. Instead, a b-galactosidase cotransfection assay (Kumar et al., 1994) was used to examine cell viability. Cells were transiently transfected with a b-galactosidase expression plasmid and the various expression vectors described above. 36 hours later cells were stained with X-gal and positive blue cells visualized and counted. In all cell lines a dramatic (~100-fold) reduction in the number of b-galactosidase-positive cells was observed for the TRADD vector compared to the control vector. When crmA and TRADD were coexpressed, the crmA effect was obvious and the number of blue HeLa and NIH-3T3 cells was the same as in the vector controls. Co-expression of crmA protected about one-third of transfected HepG2 cells from TRADD-induced cell death. As was seen in 293 cells, neither Bcl-2 nor E1B expression exerted a protective effect on TRADD-mediated apoptosis in HeLa or NIH-3T3 cells. Bcl-2 did provide partial protection for HeLa cells from the effect of TRADD overexpression.

TRADD Overexpression Activates NF-κB: Another important activity of TNF signaled by TNF-R1 is activation of the transcription factor NF-κB. To examine a possible role for TRADD in this process we performed electrophoretic mobility shift assays (EMSAs) on nuclear extracts from 293 cells 24 hours after transient transfection with the TRADD expression vector. TRADD-expressing 293 cells were found to contain a significant amount of activated NF-κB even in the absense of exogenous TNF. In contrast, specific NF-κB complexes were detected only after TNF treatment in 293 cells transfected with an empty expression vector. Supershift experiments performed with antibodies demonstrate that the major component of the activated NF-κB complex appears to be the p65:p50 heterodimer.

Dose response experiments were performed to determine if TRADD expression might lead to activation of a NF-κB-dependent reporter gene. An E-selectin-luciferase reporter construct (Schindler and Baichwal, 1994) was cotransfected with increasing amounts of the TRADD expression vector into 293 cells. TRADD expression potently activated the reporter gene with maximal luciferase activity (approx. 400-fold induction) occurring at a 0.32 mg dose of the TRADD expression vector. These levels of reporter gene induction are greater than the~20-fold induction observed when 293 cells are treated with TNF alone. Further increases in TRADD vector resulted in diminished levels of reporter activity, probably due to induction of cell death. The observed luciferase induction was dependent on NF-κB activation since TRADD expression failed to activate a control reporter construct in which the NF-κB site in the E-selectin promoter was mutated.

CrmA does not block TRADD-induced NF-κB Activation: Since crmA is a potent inhibitor of apoptosis induced by either TNF treatment (Tewari and Dixit, 1995) or TRADD expression, we were interested in examining its effect on NF-κB activation. To do this, 293 cells were cotransfected with the E-selectin reporter construct and expression vectors for trinA, TRADD, or both. CrmA expression had little or no effect on TRADD-induced NF-κB activation in 293 cells as determined by either EMSA or the luciferase reporter gene assay.

HeLa and HepG2 cells were also examined for NF-κB activation following transient transfection with the TRADD expression vector alone. In most experiments no activation was seen in these cell lines, a result potentially attributable to rapid induction of cell death. To determine whether NF-κB could be activated by TRADD if cell death were inhibited, these cell lines were cotransfected with crmA and TRADD expression vectors. While crmA expression alone had no effect, substantial activation of NF-κB was observed in the crmA/TRADD cotransfection experiments. These results demonstrate an inherent ability of TRADD to activate NF-κB, which can be more readily observed if the death pathway is blockaded by crmA expression.

Deletion Mutagenesis of TRADD: The experiments described thus far have identified four distinct properties of TRADD: (i) interaction with TNF-R1; (ii) self-association; (iii) induction of apoptosis; and (iv) activation of NF-κB. To ascertain whether these properties reside in common or distinct domains of TRADD, we constructed myc-tagged expression vectors for a series of N- and C-terminal deletion mutants. The ability of each mutant to induce apoptosis was determined in the 293 transient assay described above. A TRADD mutant (Δ1–194) containing only 118 C-terminal amino acids was able to trigger cell death, whereas a mutant (Δ1–204) ten amino acids shorter did not. Deleting from the C-terminus, a mutant (Δ301–312) lacking only 12 residues was inactive, but a mutant (Δ306–312) lacking seven amino acids retained the ability to induce apoptosis of 293 cells. This analysis localized the apoptosis activation function (death domain) of TRADD to a 111 residue region extending from amino acid 195 to 305. NF-κB activation for each TRADD mutant was determined in the NF-κB reporter co-transfection assay. By this analysis the region of TRADD required for NF-κB activation was strictly concordant with that required for apoptosis.

The TRADD deletion routants were assayed for association with TNF-R1 by measuring the interaction of $^{35}$S-labeled in vitro translated mutants with a GST-TNF-R1 fusion protein. Two mutants (Δ306–312 and Δ1–194) bound as well as wild-type TRADD to TNF-R1. These same two mutants were biologically active as determined by the apoptosis and NF-κB activation assays. TRADD mutants that were inactive in these biological assays bound TNF-R1 poorly, or not at all.

The ability of the TRADD deletion mutants to self-oligomerize was assessed by binding experiments between a GST-TRADD fusion protein and the in vitro translated mutants. The same routants that interacted with GST-TNF-R1 were able to bind GST-TRADD, although by this assay self-association was much weaker than interaction with TNF-R1. The one difference observed was that the biologically inactive Δ301–312 mutant, which does not interact with TNF-R1, was still able to self-associate. These results demonstrate that a 111 amino acid domain (aa 195–305) of TRADD is capable of oligomerization, TNF-R1 interaction, stimulation of programmed cell death and NF-κB activation.

Death Domains of TRADD and TNF-R1 Share Sequence Similarity

Database screens failed to identify any proteins bearing significant similarity to the primary amino acid sequence of TRADD. However, since the 111 amino acid death domain of TRADD shares many properties with the~80 amino acid death domain of TNF-R1, these two sequences were directly compared. Alignment of TRADD residues 196–302 relative to residues 319–425 of TNF-R1 results in 25 identities over 107 amino acids (23%). The most obvious sequence similarity was found in the stretch of 68 amino acids (TRADD residues 222–289 and TNF-R1 residues 345–412). If a single gap is introduced in both sequences (after TRADD 235 and after TNF-R1 364), 22 identities (32%) and 21 conservative changes are found. Whereas the majority of the identities are leucines and arginines, three observations indicate that the sequence similarity may be functionally significant: (i) six amino acids have been identified in the death domain of TNF-R1 that, when mutated to alanine, abolish signaling (Tartaglia et al., 1993b). Five of these six amino acids, which extend to both ends of the aligned sequence, are identical or highly conserved in TRADD; (ii) the sequence similarity between TRADD and TNF-R1 over this region is roughly the same as that between the functionally similar death domains of TNF-R1 and Fas antigen; and (iii) TRADD and Fas antigen, which appear not to interact with each other, share only 9 identities (13%) over these 68 residues.

Reagents and Cell Lines: Recombinant human TNF (specific activity>$10^7$ units/mg) was provided by Genentech, Inc. The rabbit anti-TNF-R1 polyclonal antibody was described previously (Tartaglia et al., 1991). The rabbit anti-TRADD antiserum was raised against a GST-TRADD fusion protein by BAbCO (Richmond, Calif.). Rabbit anti-p50 and anti-p65 polyclonal antibodies were purchased from Santa Cruz Biotechnology. The HtTA-1 (HeLa expressing a tetracycline-controlled transactivator; Hermann Bujard), 293 (Robert Tjian), HepG2 (American Type Culture Collection [ATCC]), ECV304 (ATCC), and NIH-3T3 (Steve McKnight) cell lines were obtained from the indicated sources.

Expression Vectors

The TRADD cDNA was cloned as a 1.4 kb EcoRI fragment into pRK5 under the transcriptional control of the cytomegalovirus (CMV) immediate early promoter-enhancer (Schall et al., 1990). The resulting plasmid pRK-TRADD was used for mammalian cell expression and for in vitro transcription and translation using the SP6 promoter. Myc epitope-tag constucts were made by replacing the eight N-terminal codons of TRADD with DNA encoding the sequence M-A-S-M-E-Q-K-L-I-S-E-E-D-L (SEQUENCE ID NO:5). C-terminal deletion mutants of TRADD were generated by replacement of sequences between the XhoI site in TRADD and the HindIII site in pRK5 with synthetic DNA containing the appropriate coding sequence and in-frame stop codons. N-terminal deletion constructs of TRADD were generated by PCR and contained the N-terminal myc epitope-tag sequence. The various mutant TNF-R1 expression vectors were described previously (Tartaglia et at., 1993$b$). A plasmid containing the cowpox virus crmA gene is described in Pickup et at., 1986. A 1.0 kb crmA fragment was generated by PCR and inserted into the pRK5 vector to give the plasmid pRK-crmA. The Bcl-2 expression vector pSFFV-Bcl-2 was based on the long terminal repeat of the splenic focus-forming virus. The NF-κB-luciferase reporter plasmid pELAM-luc, containing E-selectin promoter sequences from position −730 to +52 is described in Schindler and Baichwal, 1994.

Yeast Two-Hybrid Cloning

DNA encoding the intracellular domain (amino acids 214–426) of TNF-R1 was cloned into the yeast GAL4 DNA binding domain vector pGBT9. The resulting plasmid pGAL4$bd$-TNF-R1$icd$ used as bait in two-hybrid screens of HeLa and B cell cDNA libraries (Clontech) following the Matchmaker Two-Hybrid System. Protocol (Clontech). Briefly, the $S.$ $cerevisiae$ indicator strain HF7c was transformed sequentially with the bait plasmid and a cDNA library. Positive yeast clones were selected by prototrophy for histidine and expression of b-galactosidase. Yeast DNA was recovered and transformed into $E.$ $coli$. Plasmids containing cDNA clones were identified by restriction mapping and further characterized by DNA sequencing. Subsequent two-hybrid interaction analyses were carried out by cotransformation of plasmids containing the GAL4 DNA binding (pGBT9) and activation (pGAD424) domains into $S.$ $cerevisiae$ strain SFY526. Assays for b-galactosidase activity were performed using CPRG as substrate (Iwabuchi et al., 1993).

cDNA Cloning and Northern-Hybridization

The cDNA insert of approximately 1 kb from two-hybrid clone B27 was used as probe to screen human HeLa and umbilical vein endothelial cell (HUVEC) cDNA libraries in lgt11 (provided by Dr. Zhaodan Cao; complexity of>2×10$^6$ clones each) by standard methods (Sambrook et al., 1989). Two independent positive clones were obtained from each library. Following subcloning into pBluescript KS (Stratagene) DNA sequencing was performed on an ABI model 373A automated DNA sequencer using the Prism Dye Terminator Cycle sequencing kit (Applied Biosystems). Northern analysis of the human multiple tissue blot (Clontech) was performed according to the manufacturer's instructions using an~400bp EcoRI-NarI fragment from the 5' end of TRADD cDNA as probe.

Cell Culture, Transfections and Reporter Assays 293 and NIH-3T3 cells were maintained in high glucose DMEM medium containing 10% FCS, 100 mg/ml penicillin G and 100 mg/ml streptomycin (Gibco). HtTA-1 (HeLa) cells were grown in the same medium containing 400 mg/ml G418. HepG2 cells were maintained in DMEM/F12 (1:1) medium with the same additives. For reporter assays, co-immunoprecipitations, and cell killing assays,~2×10$^5$ cells/well were seeded on 6-well (35 mm) dishes and grown in 5% CO$_2$ at 37° C. The following day, cells were tranfected by the calcium phosphate precipitation method (Ausubel et al., 1994). The control vector pRK5 was used as carrier DNA so that all transfections in a given experiment contained equal amounts of total DNA. After an incubation of 24–36 hours, cells were washed twice with PBS and then lysed with 200 ml lysis buffer (25 mM Tris-phosphate pH 7.8, 2 mM DTT, 2 mM 1,2-diaminocyclohexane-N,N,N',N'-tetraacetic acid, 10% glycerol, 1% triton X-100). 20 ml aliquots of cell lysates were mixed with 100 ml of luciferase assay reagent (Promega) and the luciferase activity determined using a Model 20$e$ luminometer (Turner Designs). b-galactosidase activity was determined in a mixture containing 10 ml of cell lysate, 10 ml of 50 mM CPRG (chlorophenol red b-D-galactopyranoside) and 80 ml of Z buffer (60 mM Na$_2$HPO$_4$, 10 mM KC, 1 mM b-mercaptoethanol, pH 7.0). Samples were incubated at 37° C. until red color developed and absorbance determined at 574 nm. These values were used to normalize transfection efficiencies. For DNA laddering and EMSA experiments large scale transfections were performed using 100 mm dishes seeded with~10$^6$ cells. 24–36 hours after transfection, DNA or nuclear extracts were prepared as described below.

Co-Immunoprecipitations and Western Analysis

Western analysis to detect TRADD was performed with the anti-TRADD antiserum and horseradish peroxidase-coupled goat anti-rabbit IgG (Amersham) using enhanced chemiluminescence according to the manufacturer's protocol. For immunoprecipitation assays, 50 ml aliquots of lysates from transfected cells were incubated with 1 ml of the anti-TNF-R1 antibody and 450 ml E1A buffer (50 mM Hepes pH 7.6, 250 mM NaCl, 0.1% NP-40, 5 mM EDTA). The mixture was incubated at 4° C. for 1 hour, then mixed with 20 ml of a 1:1 slurry of protein A sepharose (Pharmacia) and incubated for another hour. The beads were washed twice with 1 ml E1A buffer, twice with 1 ml high salt (1M NaCl) E1A buffer, and twice again with E1A buffer. The precipitates were fractionated on 10% SDS-PAGE and then transferred electrophoretically to Immobilon-P membrane (Millipore). The blot was then subjected to Western analysis with anti-myc monoclonal antibody and horseradish peroxidase-coupled rabbit anti-mouse Ig (Amersham) as described above.

Generation of GST Fusion Proteins and in Vitro Binding Assays

TRADD and the cytoplasmic regions of TNF-R1, TNF-R1(−20), Fas antigen, IL1-R1, TNF-R2 were expressed individually as GST (glutathione-S-transferase) fusion proteins using pGEX vectors (Pharmacia). Expression and purification of the GST fusion proteins were performed as described (Smith and Johnson, 1988). $^{35}$S-labeled proteins were generated using the TNT SP6 Coupled Reticulocyte Lysate System (Promega) and the various TRADD expression constructs in pRK5. For each in vitro binding assay, 10 ml of glutathione sepharose beads (Pharmacia) bound to the appropriate GST fusion protein (~5 mg) was incubated with $^{35}$S-labeled polypeptides (equivalent cpm as determined by phosphorimager) in 1 ml of E1A buffer at 4° C. for one hour. The beads were then washed six times with E1A buffer. Proteins on the beads were fractionated by SDS-PAGE and exposed to Kodak X-ray film following drying of the gel.

Apoptosis Assays

DNA fragmentation assays were performed essentially as described (Hermann et al., 1994). Briefly, approximately $10^7$ transfected or nontransfected cells were washed with PBS, pelleted and lysed in 20 mM EDTA, 50 mM Tris-HCl (pH 7.5) containing 1% NP-40. After a 5 min centrifugation at 1600×g, the supernatant was brought to 1% SDS, and treated 2 hr with 5 mg/ml RNase A at 56° C. and 2 hr with 2.5 mg/ml proteinase K at 37° C. The mixture was extracted with phenol/chloroform, DNA was ethanol precipitated and 150 ng DNA aliquots were fractionated by electorphoresis in a 1.6% agarose gel.

β-galactosidase cotransfection assays for determination of cell death were performed as described by Kumar et al. (1994). Transfected cells were washed with PBS; fixed at 4° C. for 5 min in PBS containing 2% paraformaldehyde, 0.2% gluteraldehyde, washed again with PBS, and stained for at least 3 hours with PBS containing 1 mg/ml X-gal, 5 mM potassium ferricyanide, 5 mM potassium ferrocyanide, 2 mM $MgCl_2$, 0.02% NP-40, 0.01% SDS. Cells were observed microscopically and the number of blue cells per 35 mm well was determined by counting. At least three independent transfections were performed for each set of conditions.

Electrophoretic Mobility Shift Assays

Nuclear extracts were prepared as described by Osborn et at. (1989). Double-stranded deoxyoligonucleotides containing an NF-κB binding site were $^{32}P$-labeled using polynucleotide kinase. Each gel shift assay was performed in a 30 ml reaction mixture, which contained 10 mg nuclear extracts, 0.4 ng of radiolabeled oligonucleotide probe, 1 mg of sonicated $E.\ coli$ DNA, 6 ml of 5 X EMSA buffer (100 mM Hepes pH 7.6, 250 mM KCl, 5 mM DTT, 5 mM EDTA, 25% glycerol), and where necessary, 20 mg of cold competitor oligonucleotides. Mixtures were incubated at room temperature for 10 minutes and then subjected to electrophoretic fractionation on a 5% polyacrymide gel at 4° C.

Cited References

Ausubel et at. (1994) Current Protocols in Molecular Biology (New York: Greene Publishing Associates/Wiley & Sons, Inc.); Beg et at. (1993) *Genes Dev.* 7:2064–2070; Beg et at. (1993) *Molec. and Cell. Biol.* 1993:3301–3310; Boldin et al. (1995) *J. Biol. Chem.* 270:387–391; Darnell et al. (1994) *Science* 264:1415–1421; Englemann et al. (1990) *J. Biol. Chem.* 265:14497–14504; Erickson et al. (1994) *Nature* 372:560–563; Espevik et at. (1990) *J. Exp. Med.* 171:415–426; Fantl et al. (1993) *Ann. Rev. Blochem.* 62:453–482; Fields and Song (1989) *Nature* 340:245–246; Gagliardini et al. (1994) *Science* 263:826–828; Gehr et al. (1992) *J. Immunol.* 149:911–917; Goodwin et al. (1991) *Mol. Cell. Biol.* 11:3020–3026; Hermann et al. (1994) *Nucl. Acids Res.* 22:5506–5507; Hu et al. (1994) *J. Biol. Chem.* 269:30069–30072; Itoh et al. (1993) *J. Biol. Chem.* 268:10932–10937; Iwabuchi et al. (1993) *Oncogene* 8:1693–1696; Jacobsen et al. (1994) *Proc. Natl. Acad. Sci. USA* 91:10695–10699; Kishimoto et al. (1994) *Cell* 76:253–262; Kruppa (1992) *J. Immunol.* 148:3152–3157; Kumar et al. (1994) *Genes & Devel.* 8:1613–1626; Lægreid et al. (1994) J. Biol. Chem. 269:7785–7791; Lewis et al. (1991) *Proc. Natl. Acad. Sci. USA* 88:2830–2834; Liou and Baltimore (1993) *Curr. Opin. Cell Biol.* 5:477–487; Loetscher (1990) *Cell* 61:351–359; Miura et al. (1993) *Cell* 75:656–660; Osborn et at. (1989) *Proc. Natl. Acad. Sci. USA* 86:2336–2340; Palombella et al. (1994) *Cell* 78:773–785; Pfeffer et al. (1993) *Cell* 73:457–467; Pickup et al. (1986) *Proc. Natl. Acad. Sci. USA* 83:7698–7702; Ray et al. (1992) *Cell* 69:587–604; Rothe et at. (1992) *Immunol. Res.* 11:81–90; Rothe et al. (1993) *Nature* 364:798–802; Rothe et al. (1994) *Cell* 78:681–692; Sambrook et al. (1989) Molecular Cloning: A Laboratory Manual, Second Edition (Cold Spring Harbor, N.Y: Cold Spring Harbor Laboratory Press); Schall et al. (1990) *Cell* 61:361–370; Schindler and Baichwal (1994) *Mol. Cell. Biol.* 14:5820–5831; Schlessinger and Ullrich (1992) *Neuron* 9:383–391; Schulze-Osthoff et al. (1994) *EMBO J.* 13:4587–4596; Smith et at. (1990) *Science* 248:1019–1023; Smith et al. (1994) *Cell* 76:959–962; Smith and Johnson (1988) *Gene* 67:31–40; Song et al. (1994) *J. Biol. Chem.* 269:22492–22495; Tartaglia et al. (1991) *Proc. Natl. Acad. Sci. USA* 88:9292–9296; Tartaglia and Goeddel (1992) *Immunol. Today* 13:151–153; Tartaglia et al. (1993a) *J. Immunol.* 151:4637–4641; Tartaglia et al. (1993b) *Cell* 74:845–853; Tewari and Dixit (1995) *J. Biol. Chem.* 270:3255–3260; Thornberry et al. (1992) *Nature* 356:768–774; Tomei and Cope (1991) Current Communications in Cell & Molecular Biology (Cold Spring Harbor, New York: Cold Spring Harbor Laboratory Press); VanArsdale and Ware (1994) *J. Immunol.* 153:3043–3050; Vandenabeele et al. (1992) *J. Exp. Med.* 176:1015–1024; Wiegmann et al. (1994) Cell 78:1005-1015; Wong and Goeddel (1994) *J. Immunol.* 152:1751–1755; Wong et al. (1992) *J. Immunol.* 149:3550–3553; and Yuan et al. (1993) *Cell* 75:641–652.

EXAMPLES

1. Protocol for TRADD—TNF-R1 binding assay.

A. Reagents:

Neutralite Avidin: 20 μg/ml in PBS.

Blocking buffer: 5% BSA, 0.5% Tween 20 in PBS; 1 hr, RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}P$ TRADD 10x Stock: $10^{-8}$–$10^6$M "cold" TRADD supplemented with 200,000–250,000 cpm of labeled TRADD (Beckman counter). Place in the 4° C. microfridge during screening.

Protease Inhibitor Cocktail (1000X): 10 mg Trypsin Inhibitor (BMB#109894), 10 mg Aprotinin (BMB#236624), 25 mg Benzamidine (Sigma#B-6506), 25 mg Leupeptin (BMB#1017128), 10 mg APMSF (BMB#917575), and 2 mM $NaVo_3$ (Sigma#S-6508) in 10 ml of PBS.

TNF-R1 Death Domain: $10^{-8}$–$10^{-5}$M biotinylated TNF-R1 Death Domain (residues 327–412) in PBS.

B. Preparation of Assay Plates:

Coat with 120μl of stock N-Avidin per well overnight at 4° C.

Wash 2X with 200 μl PBS.

Block with 150 μl of blocking buffer.

Wash 2X with 200 μl PBS.

C. Assay:

Add 40 μl assay buffer/well.

Add 10 μl compound or extract.

Add 10 μl $^{33}P$-TRADD (20,000–25,000 cpm/0.1–10 pmoles/well =$10^{-9}$–$10^{-7}$M final concentration).

Shake at 25° C. for 15 min.

Incubate additional 45 min. at 25° C.

Add 40 μl TNF-R1 Death Domain (0.1–10 pmoles/40 ul in assay buffer)

Incubate 1 hr at RT.

Stop the reaction by washing 4X with 200 μl PBS.

Add 150 μl scintillation cocktail.

Count in Topcount.

D. Controls for all Assays (located on each plate):
  a. Non-specific binding (no TNF-RI Death Domain added)
  b. Soluble (non-biotinylated TNF-R1 Death Domain) at 80% inhibition.

1. Protocol for TRADD-TRADD binding assay.

A. Reagents:

TRADD: 20 μg/ml in PBS.

Blocking buffer: 5% BSA, 0.5% Tween 20 in PBS; 1 hr, RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P TRADD 10x Stock: $10^{-8}$–$10^{-6}$M "cold" TRADD supplemented with 200,000–250,000 cpm of labeled TRADD (Beckman counter). Place in the 4° C. microfridge during screening.

Protease inhibitor Cocktail (1000X): 10 mg Trypsin Inhibitor (BMB#109894), 10 mg Aprotinin (BMB#236624), 25 mg Benzamidine (Sigma#B-6506), 25 mg Leupeptin (BMB#1017128), 10 mg APMSF (BMB#917575), and 2 mM NaVo$_3$ (Sigma#S-6508) in 10 ml of PBS.

B. Preparation of Assay plates:

Coat with 120 μl of stock TRADD per well overnight at 4° C.

Wash 2X with 200 μl PBS.

Block with 150 μl of blocking buffer.

Wash 2X with 200 μl PBS.

C. Assay:

Add 80 μl assay buffer/well.

Add 10 μl compound or extract.

Add 10 μl $^{33}$P-TRADD (20,000–25,000 cpm/0.3 pmoles/well=$3\times10^{-9}$M final concentration).

Shake at 25° C. for 15 min.

Incubate additional 45 min. at 25° C.

Stop the reaction by washing 4X with 200 μl PBS.

Add 150 μl scintillation cocktail.

Count in Topcount.

D. Controls for all Assays (located on each plate):
  a. Non-specific binding (no stock TRADD added)
  b. cold TRADD at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated Tumor necrosis factor Receptor-1 Associated Death Domain protein (TRADD) having a sequence defined by SEQUENCE ID NO:2, or a fragment of said TRADD having a TRADD-specific binding affinity.

2. An isolated Tumor necrosis factor Receptor-1 Associated Death Domain protein (TRADD) or fragment thereof according to claim 1 having a TRADD-specific transcriptional activation activity.

3. An isolated Tumor necrosis factor Receptor-1 Associated Death Domain protein (TRADD) or fragment thereof according to claim 1 having a TRADD-specific apoptosis inducing activity.

4. An isolated Tumor necrosis factor Receptor-1 Associated Death Domain protein (TRADD) or fragment thereof according to claim 1 comprising SEQUENCE ID NO:2, residues 195–305.

5. An isolated nucleic acid encoding a Tumor necrosis factor Receptor-1 Associated Death Domain protein (TRADD) or fragment thereof according to claim 1.

6. An isolated nucleic acid encoding a Tumor necrosis factor Receptor-1 Associated Death Domain protein (TRADD) or fragment thereof according to claim 2.

7. An isolated nucleic acid encoding a Tumor necrosis factor Receptor-1 Associated Death Domain protein (TRADD) or fragment thereof according to claim 3.

8. An isolated nucleic acid encoding a Tumor necrosis factor Receptor-1 Associated Death Domain protein (TRADD) or fragment thereof according to claim 4.

9. A method of identifying lead compounds for a pharmacological agent useful in the diagnosis or treatment of disease associated with Tumor necrosis factor Receptor Associated Death Domain protein (TRADD)-dependent signal transduction, said method comprising the steps of:

forming a mixture comprising:
a TRADD or TRADD fragment according to claim 1,
a natural intracellular TRADD binding target, wherein said binding target is capable of specifically binding said TRADD or TRADD fragment, and
a candidate pharmacological agent;

incubating said mixture under conditions whereby, but for the presence of said candidate pharmacological agent, said TRADD or TRADD fragment selectively binds said binding target;

detecting the presence or absence of specific binding of said TRADD or TRADD fragment to said binding target, wherein the absence of said selective binding indicates that said candidate pharmacological agent is a lead compound for a pharmacological agent capable of disrupting TRADD-dependent signal transduction.

10. A method of identifying lead compounds for a pharmacological agent useful in the diagnosis or treatment of disease associated with Tumor necrosis factor Receptor Associated Death Domain protein (TRADD)-dependent signal transduction, said method comprising the steps of:

forming a mixture comprising:
a TRADD or TRADD fragment according to claim 4,
a natural intracellular TRADD binding target, wherein said binding target is capable of specifically binding said TRADD or TRADD fragment, and
a candidate pharmacological agent;

incubating said mixture under conditions whereby, but for the presence of said candidate pharmacological agent, said TRADD or TRADD fragment selectively binds said binding target;

detecting the presence or absence of specific binding of said TRADD or TRADD fragment to said binding target, wherein the absence of said selective binding indicates that said candidate pharmacological agent is a lead compound for a pharmacological agent capable of disrupting TRADD-dependent signal transduction.

* * * * *